United States Patent
Legrand

(10) Patent No.: US 6,444,197 B2
(45) Date of Patent: Sep. 3, 2002

(54) BLEACHING COMPOSITION FOR KERATIN FIBERS, COMPRISING A COMBINATION OF TWO POLYURETHANE POLYETHERS

(75) Inventor: Frédéric Legrand, Boulogne Billancourt (FR)

(73) Assignee: L'Oreal S.A., Paris (FR)

( * ) Notice: Subject to any disclaimer, the term of this patent is extended or adjusted under 35 U.S.C. 154(b) by 41 days.

(21) Appl. No.: 09/734,732

(22) Filed: Dec. 13, 2000

(30) Foreign Application Priority Data

Dec. 13, 1999 (FR) .............................. 99 15678

(51) Int. Cl.[7] .............................. A61K 9/00; A61K 7/06; A61K 7/135; A61K 7/11
(52) U.S. Cl. .................. 424/70.1; 424/62; 424/70.11; 424/70.16; 424/70.13; 424/70.17; 424/70.21; 424/70.22; 424/70.27; 424/70.19
(58) Field of Search .............................. 424/400, 70.1, 424/62, 70.11, 70.16, 70.13, 70.17, 70.21, 70.22, 70.27, 70.19

(56) References Cited

U.S. PATENT DOCUMENTS

| | | |
|---|---|---|
| 2,261,002 A | 10/1941 | Ritter |
| 2,271,378 A | 1/1942 | Searle |
| 2,273,780 A | 2/1942 | Dittmar |
| 2,375,853 A | 5/1945 | Kirby et al. |
| 2,388,614 A | 11/1945 | Kirby et al. |
| 2,454,547 A | 11/1948 | Bock et al. |
| 2,528,378 A | 11/1950 | Mannheimer |
| 2,781,354 A | 2/1957 | Mannheimer |
| 2,961,347 A | 11/1960 | Floyd |
| 3,206,462 A | 9/1965 | McCarty |
| 3,227,615 A | 1/1966 | Korden |
| 3,589,578 A | 6/1971 | Kamphausen |
| 3,632,559 A | 1/1972 | Matter et al. |
| 3,836,537 A | 9/1974 | Boerwinkle et al. |
| 3,874,870 A | 4/1975 | Green et al. |
| 3,912,808 A | 10/1975 | Sokol |
| 3,917,817 A | 11/1975 | Vanlerberghe et al. |
| 3,929,990 A | 12/1975 | Green et al. |
| 3,966,904 A | 6/1976 | Green et al. |
| 4,001,432 A | 1/1977 | Green et al. |
| 4,005,193 A | 1/1977 | Green et al. |
| 4,013,787 A | 3/1977 | Varlerberghe et al. |
| 4,025,617 A | 5/1977 | Green et al. |
| 4,025,627 A | 5/1977 | Green et al. |
| 4,025,653 A | 5/1977 | Green et al. |
| 4,026,945 A | 5/1977 | Green et al. |
| 4,027,020 A | 5/1977 | Green et al. |
| 4,031,307 A | 6/1977 | DeMartino et al. |
| 4,079,028 A | 3/1978 | Emmons et al. |
| 4,131,576 A | 12/1978 | Iovine et al. |
| 4,155,892 A | 5/1979 | Emmons et al. |
| 4,157,388 A | 6/1979 | Christiansen |
| 4,165,367 A | 8/1979 | Chakrabarti |
| 4,172,887 A | 10/1979 | Vanlerberghe et al. |
| 4,180,491 A | 12/1979 | Kim et al. |
| 4,189,468 A | 2/1980 | Vanlerberghe et al. |
| 4,197,865 A | 4/1980 | Jacquet et al. |
| 4,217,914 A | 8/1980 | Jacquet et al. |
| 4,240,450 A | 12/1980 | Grollier et al. |
| 4,349,532 A | 9/1982 | Vanlerberghe et al. |
| 4,390,689 A | 6/1983 | Jacquet et al. |
| 4,591,610 A | 5/1986 | Grollier |
| 4,702,906 A | 10/1987 | Jacquet et al. |
| 4,719,282 A | 1/1988 | Nadolsky et al. |
| 4,761,273 A | 8/1988 | Grollier et al. |
| 4,839,166 A | 6/1989 | Grollier et al. |
| 4,996,059 A | 2/1991 | Grollier et al. |
| 5,089,252 A | 2/1992 | Grollier et al. |
| 5,281,654 A | 1/1994 | Eisenhart et al. |
| 5,888,484 A | 3/1999 | Schmitt et al. |

FOREIGN PATENT DOCUMENTS

| | | |
|---|---|---|
| EP | 0 080 976 | 6/1983 |
| EP | 0 337 354 | 10/1989 |
| EP | 0 778 020 | 6/1997 |
| EP | 0 852 943 | 7/1998 |
| FR | 1 400 366 | 12/1965 |
| FR | 1 492 597 | 8/1967 |
| FR | 1 583 363 | 10/1969 |
| FR | 2 077 143 | 10/1971 |
| FR | 2 080 759 | 11/1971 |
| FR | 2 162 025 | 7/1973 |
| FR | 2 190 406 | 2/1974 |
| FR | 2 252 840 | 6/1975 |
| FR | 2 270 846 | 12/1975 |
| FR | 2 280 361 | 2/1976 |
| FR | 2 316 271 | 1/1977 |
| FR | 2 320 330 | 3/1977 |
| FR | 2 336 434 | 7/1977 |
| FR | 2 368 508 | 5/1978 |
| FR | 2 383 660 | 10/1978 |
| FR | 2 393 573 | 1/1979 |
| FR | 2 413 907 | 8/1979 |
| FR | 2 470 596 | 6/1981 |
| FR | 2 505 348 | 11/1982 |
| FR | 2 519 863 | 7/1983 |
| FR | 2 542 997 | 9/1984 |
| FR | 2 598 611 | 11/1987 |
| WO | WO 97/24108 | 7/1997 |
| WO | WO 99/36047 | 7/1999 |

OTHER PUBLICATIONS

M.R. Porter, "Handbook of Surfactants", Blackie & Son Ltd., Glasgow & London, 1991, pp. 117–178.
English language Derwent Abstract of EP 0 080 976.
English language Derwent Abstract of FR 2 077 143.
English language Derwent Abstract of FR 2 080 759.
English language Derwent Abstract of FR 2 320 330.
English language Derwent Abstract of FR 2 336 434.

*Primary Examiner*—Thurman K. Page
*Assistant Examiner*—S. Howard
(74) *Attorney, Agent, or Firm*—Finnegan, Henderson, Farabow, Garrett & Dunner, L.L.P.

(57) ABSTRACT

Bleaching compositions comprising at least one oxidizing agent and at least one combination of two polyurethane polyethers. Processes and devices for bleaching using the aforesaid compositions.

67 Claims, No Drawings

BLEACHING COMPOSITION FOR KERATIN FIBERS, COMPRISING A COMBINATION OF TWO POLYURETHANE POLYETHERS

The present invention relates to a composition for bleaching keratin fibers, for example, human keratin fibers such as the hair, comprising at least one oxidizing agent and at least one combination of two specific polyurethane polyethers.

Keratin fibers, for example human hair, may be bleached with at least one bleaching composition comprising at least one oxidizing agent. An example of an oxidizing agent typically used is hydrogen peroxide. Other non-limiting examples of oxidizing agents include compounds capable of producing hydrogen peroxide by hydrolysis, such as, for example, urea peroxide and persalts. Non-limiting examples of persalts include persalts chosen from perborates, percarbonates and persulphates.

The at least one bleaching composition may, for example, be in the form of at least one anhydrous product, such as anhydrous products chosen from powders and creams, comprising at least one alkaline compound, for example, compounds chosen from alkaline silicates and amines, and at least one peroxygenated reagent which may be diluted at the time of use with an aqueous hydrogen peroxide composition.

Non-limiting examples of peroxygenated reagents include peroxygenated reagents chosen from ammonium and alkali metal persulphates, perborates and percarbonates.

The bleaching compositions may also, for example, result from mixing, at the time of use, at least one anhydrous powder of peroxygenated reagent with at least one aqueous composition comprising at least one alkaline compound and at least one aqueous composition comprising hydrogen peroxide.

Bleaching compositions can also be in the form of ready-to-use thickened aqueous hydrogen peroxide compositions.

As used herein, "ready-to-use composition" refers to compositions intended to be applied in an unmodified form to the keratin fibers. These compositions may include, for example, compositions that can be stored in an unmodified form before use and compositions that can result from mixing at least two compositions at the time of use.

At least one thickener, such as, for example, thickeners chosen from crosslinked polyacrylic acid, hydroxyethylcelluloses, certain polyurethanes, and waxes, may be used to localize the bleaching product to the application to the hair in order for it not to run down the face or beyond the areas which it is proposed to bleach. Also, in the case of aqueous bleaching compositions, mixtures of at least one nonionic surfactant with an HLB (Hydrophilic Lipophilic Balance) value, can give rise to a gelling effect when the at least one non-ionic surfactant is suitably chosen and diluted with at least one diluent chosen from water and surfactants.

However, it has been found that the thickening systems mentioned above may produce bleaching results that may not be sufficiently powerful and homogeneous. Such systems may also leave the hair coarse.

Moreover, it has been found that ready-to-use bleaching compositions comprising the at least one oxidizing agent and also the thickener systems of the prior art may not allow a sufficiently precise application without running, and may fall in viscosity over time.

However, the inventors have discovered that it is possible to obtain ready-to-use bleaching compositions which do not run and thus remain satisfactorily localized at the point of application. These compositions also make it possible to obtain powerful and homogeneous bleaching results while at the same time leaving the hair less coarse.

The present invention therefore relates to a ready-to-use composition for bleaching keratin fibers, for example, human keratin fibers such as the hair, comprising, in a medium appropriate for bleaching, at least one ("at least one" is used in its normal sense to denote one or more) oxidizing agent, wherein said composition also comprises at least one combination of at least:

one polyurethane polyether (a) which can be obtained by polycondensation of at least three compounds comprising (i) at least one polyethylene glycol generally comprising from 50 to 500 mol of ethylene oxide, (ii) at least one $C_8$–$C_{30}$ fatty alcohol, and (iii) at least one diisocyanate and, one polyurethane polyether (b) which can be obtained by polycondensation of at least three compounds comprising (i) at least one polyethylene glycol generally comprising from 50 to 500 mol of ethylene oxide, (ii) at least one $C_8$–$C_{30}$ fatty alcohol other than that of the at least one polyurethane polyether (a), and (iii) at least one diisocyanate.

In one embodiment, the at least one polyurethane polyether (a) and the at least one polyurethane polyether (b) can be used, wherein the at least one polyethylene glycol is chosen from polyethylene glycols generally comprising 150 and 180 mol of ethylene oxide. In addition, the at least one polyurethane polyether (a) and the at least one polyurethane polyether (b) can be, for example, combined with saccharide such as maltodextrin. As a further example, the at least one polyurethane polyether (a) and the at least one polyurethane polyether (b) can be used wherein the at least one diisocyanate is methylenebis(4-cyclohexyl isocyanate).

Another embodiment of the invention includes bleaching compositions as defined above, wherein at least one polyurethane polyether (a) is obtained by polycondensation of at least three compounds chosen from compounds comprising at least one polyethylene glycol chosen from polyethylene glycols generally comprising 150 and 180 mol of ethylene oxide, stearyl (C18) alcohol and methylenebis(4-cyclohexyl isocyanate), and at least one polyurethane polyether (b) is obtained by polycondensation of at least three compounds -chosen from compounds comprising at least one polyethylene glycol chosen from polyethylene glycols generally comprising 150 and 180 mol of ethylene oxide, decyl (C10) alcohol and methylenebis(4-cyclohexyl isocyanate).

Among the at least one polyurethane polyether (a), mention may be made of the product sold by the company Rohm & Haas under the trade name: Aculyn 46, which is a polycondensate comprising, as elements, at least one polyethylene glycol chosen from polyethylene glycols generally comprising 150 and 180 mol of ethylene oxide, stearyl alcohol and methylenebis(4-cyclohexyl isocyanate) (SMDI), at 15% by weight in a matrix of maltodextrin (4%) and water (81%).

Among the at least one polyurethane polyether (b), mention may be made of the product sold by the company Rohm & Haas under the trade name: Aculyn 44, which is a polycondensate comprising, as elements, at least one polyethylene glycol chosen from polyethylene glycols generally comprising 150 and 180 mol of ethylene oxide, decyl alcohol and methylenebis(4-cyclohexyl isocyanate) (SMDI), at 35% by weight in a mixture of propylene glycol (39%) and water (26%).

According to the present invention, when the ready-to-use composition results from the mixing of several compositions at the time of use, the combination of the at least one polyurethane polyether (a) and the at least one polyurethane polyether (b) may be present in at least one of the mixed compositions.

As a result, the combination of the at least one polyurethane polyether (a) and the at least one polyurethane polyether (b) may be present in an anhydrous composition in the form of powder, for example, a pulverulent powder.

The combination of the at least one polyurethane polyether (a) and the at least one polyurethane polyether (b) may additionally be present, for example, in the form of a cream.

According to the present invention, the combination of the at least one polyurethane polyether (a) and the at least one polyurethane polyether (b) may be present in at least one aqueous composition which may be mixed at the time of use with an anhydrous composition in a form chosen from powders and creams containing at least one oxidizing agent.

In an embodiment of the invention, at least one aqueous composition is mixed with at least one anhydrous composition comprising hydrogen peroxide.

The invention is also directed towards a process for bleaching keratin fibers, for example, human keratin fibers such as the hair, using the ready-to-use bleaching composition as described.

The invention is also directed towards bleaching devices or packing "kits" comprising such a ready-to-use composition.

For example, a two-compartment device may comprise a first compartment comprising at least one of the following chosen from: powders, anhydrous creams, and aqueous compositions; the second compartment comprises at least one aqueous composition; at least one of the two compartments comprises at least one oxidizing agent and at least one of the two compartments comprises at least one combination defined above of at least one polyurethane polyether (a) and at least one polyurethane polyether (b).

Another multi-compartment "kit" may, for example, comprise a first compartment comprising at least one of the following chosen from: anhydrous powders and creams and further comprise two other compartments, each comprising at least one aqueous composition; at least one of the three compartments comprising at least one oxidizing agent and at least one of the three compartments comprising at least one combination defined above of at least one polyurethane polyether (a) and at least one polyurethane polyether (b).

According to the present invention, the at least one polyurethane polyether (a) and the at least one polyurethane polyether (b) may, by way of example, be prepared according to the processes disclosed in U.S. Pat. Nos. 4,079,028, 4,180,491, 4,155,892 and 5,281,654, the disclosures of which are incorporated by reference herein.

According to the present invention, the amount by weight, relative to the total weight of the composition, of the at least one polyurethane polyether (a) can, for example, generally range from 0.01% to 5%, such as from 0.02% to 2%; the amount of the at least one polyurethane polyether (b) can, for example, generally range from 0.01% to 5%, such as, for example, from 0.02% to 2%. The weight ratio of the at least one polyurethane polyether (a) to the at least one polyurethane polyether (b) can, for example, generally range from 0.1:1 to 10:1, such as, for example, from 0.5:1 to 5:1.

According to the present invention, oxidizing agents which may be used can, for example, be chosen from hydrogen peroxide and compounds which release hydrogen peroxide by hydrolysis, such as, for example, urea peroxide and persalts.

According to the present invention, persalts which may be used may include, for example, persalts chosen from persulphates and perborates. Non-limiting examples of persulphates include sodium persulphate and potassium persulphate.

Other oxidizing agents may include, for example, chlorites.

An enzymatic system which generates oxidizing species, for example, hydrogen peroxide, may also be used. Non-limiting examples of such enzymatic systems which may be used include two-electron oxidoreductases combined with their donor in the presence of air, and the system: uricase, uric acid and air.

At least one organic peroxide may also be used.

The concentration of hydrogen peroxide in the ready-to-use compositions may, for example, generally range from 2 to 40 volumes. The concentration of other oxidizing compounds including, for example, the compounds capable of forming hydrogen peroxide by hydrolysis, can, for example, generally range from 0.1% to 25% by weight relative to the total weight of the composition.

The composition according to the invention may also comprise at least one direct dye, in addition to the oxidizing agents defined above. These direct dyes may, for example, be chosen from nitro dyes, azo dyes and anthraquinone dyes, whether of neutral, acidic or cationic nature.

In addition, the compositions according to the invention may also comprise at least one polymer chosen from cationic and amphoteric polymers, such as substantive polymers.

As used herein, "cationic polymer" refers to polymers chosen from polymers comprising at least one cationic group and polymers comprising at least one group that can be ionized to form cationic groups.

The cationic polymers which may be used in accordance with the present invention may be chosen from any of those already known to improve at least one cosmetic property of hair, such as, for example, those described in patent application EP-A-0 337,354 and in French patent application Nos. FR-A-2,270,846, 2,383,660, 2,598,611, 2,470,596 and 2,519,863, the disclosures of which are incorporated herein by reference.

According to the present invention, the at least one cationic polymer may be chosen from polymers which comprise at least one unit comprising at least one group chosen from primary amine groups, secondary amine groups, tertiary amine groups and quaternary amine groups, wherein said at least one group forms part of the polymer skeleton, or is carried by at least one lateral substituent on said polymer skeleton.

According to the present invention, the at least one cationic polymer has a number-average molecular mass generally ranging from 500 to $5 \times 10^6$, such as from $1 \times 10^3$ to $3 \times 10^6$.

The at least one cationic polymer may be chosen from polymers of quaternary polyammonium type, polymers of polyamino amide type and polymers of polyamine type. Such types of polymers are known in the art. They are described in French patents Nos. 2,505,348 and 2,542,997, the disclosures of which are incorporated herein. Non-limiting examples of such polymers include:

(1) homo- and co-polymers derived from at least one monomer chosen from acrylic esters, methacrylic esters and amides, wherein said homo- and co-polymers comprise at least one unit chosen from the units of the formulae:

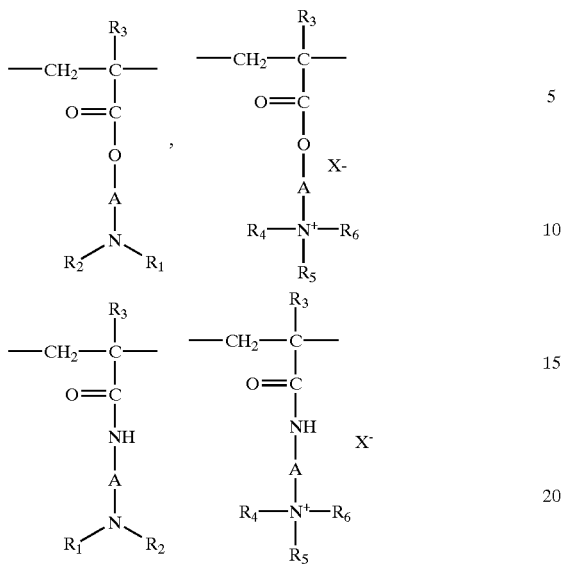

wherein $R_3$, which may be identical or different, are each chosen from hydrogen and $CH_3$ groups;

A, which may be identical or different, are each chosen from linear and branched alkyl groups comprising 1 to 6 carbon atoms, such as 2 or 3 carbon atoms, and hydroxyalkyl groups comprising from 1 to 4 carbon atoms;

$R_4$, $R_5$ and $R_6$, which may be identical or different, are each chosen from alkyl groups comprising from 1 to 18 carbon atoms, such as from 1 to 6 carbon atoms, and benzyl groups;

$R_1$ and $R_2$, which may be identical or different, are each chosen from hydrogen atoms and alkyl groups comprising from 1 to 6 carbon atoms, such as methyl and ethyl;

$X^-$ is an anion chosen from anions derived from at least one inorganic acid and anions derived from at least one organic acid, such as methosulfate anions and halides, such as chlorides and bromides.

Polymers of family (1) may further comprise at least one unit derived from at least one comonomer chosen from vinyllactams, vinyl esters, acrylamides, methacrylamides, diacetone acrylamides, acrylamides and methacrylamides substituted on the nitrogen with at least one group chosen from ($C_1$–$C_4$) alkyls, acrylic acids, methacrylic acids, acrylic esters, and methacrylic esters. Non-limiting examples of vinyllactams include vinylpyrrolidone and vinylcaprolactam.

Non-limiting examples of suitable copolymers are:

copolymers derived from at least one monomer of (i) acrylamide and (ii) dimethylaminoethyl methacrylate quaternized with at least one group chosen from dimethyl sulphate and dimethyl halide, such as the product sold under the name Hercofloc by the company Hercules;

copolymers derived from at least one monomer of (i) acrylamide and (ii) methacryloyloxyethyltrimethylammonium chloride described, for example, in patent application EP-A-080,976, the disclosure of which is incorporated herein by reference, and which is sold under the name Bina Quat P 100 by the company Ciba Geigy;

copolymers derived from at least one monomer of (i) acrylamide and (ii) methacryloyloxyethyltrimethylammonium methosulphate, such as, for example, copolymers sold under the name Reten by the company Hercules;

quaternized and non-quaternized vinylpyrrolidone/dialkylaminoalkyl acrylate copolymers and quaternized and non-quaternized vinylpyrrolidone/dialkylaminoalkyl methacrylate copolymers, such as the products sold under the name "Gafquat" by the company ISP, such as, for example, "Gafquat 734" or "Gafquat 755" and the products known as "Copolymer 845, 958 and 937". These polymers are described in detail in French patents 2,077,143 and 2,393,573, the disclosures of which are incorporated herein by reference;

dimethylaminoethyl methacrylate/vinylcaprolactam/vinylpyrrolidone terpolymers, such as the product sold under the name Gaffix VC713 by the company ISP;

vinylpyrrolidone/methacrylamidopropyldimethylamine copolymers, such as the product sold under the name Styleze CC10 by ISP; and quaternized vinylpyrrolidone/dimethylaminopropylmethacrylamide copolymers, such as the product sold under the name "Gafquat HS 100" by the company ISP;

(2) cellulose ether derivatives comprising quaternary ammonium groups, such as those described in French patent 1,492,597, the disclosure of which is incorporated herein by reference, and polymers sold under the names "JR" (JR 400, JR 125 and JR 30M) and "LR" (LR 400, or LR 30M) by the company Union Carbide Corporation. These polymers are also defined in the CTFA dictionary as quaternary ammoniums of hydroxyethylcellulose which has reacted with an epoxide substituted with a trimethylammonium group;

(3) cationic cellulose derivatives such as cellulose copolymers and cellulose derivatives grafted with at least one water-soluble monomer of quaternary ammonium, such as those described in U.S. Pat. 4,131,576, the disclosure of which is incorporated herein by reference, such as hydroxyalkylcelluloses (such as, for example, hydroxymethylcelluloses, hydroxyethylcelluloses and hydroxypropylcelluloses, wherein said hydroxyalkylcelluloses are grafted with at least one salt chosen from, for example, methacryloylethyltrimethylammonium salts, methacrylamidopropyltrimethylammonium salts and dimethyldiallylammonium salts). For example, commercial products corresponding to the aforementioned cationic cellulose derivatives include the products sold under the names "Celquat L 200" and "Celquat H 100" by the company National Starch;

(4) cationic polysaccharides, such as those described in U.S. Pat. Nos. 3,589,578 and 4,031,307, the disclosures of which are incorporated herein by reference, such as guar gums comprising at least one cationic trialkylammonium group. For example, guar gums modified with at least one salt, such as a chloride salt, of 2,3-epoxypropyltrimethylammonium may be used in the present invention. Such products are sold, for example, under the trade names Jaguar C13 S, Jaguar C 15, Jaguar C 17 and Jaguar C162 by the company Meyhall.

(5) polymers comprising (i) at least one piperazinyl unit and (ii) at least one group chosen from divalent alkylene groups and divalent hydroxyalkylene groups, wherein said at least one group optionally comprises at least one chain chosen from straight chains and branched chains, wherein said at least one chain is optionally interrupted by at least one entity chosen from oxygen atoms, sulphur atoms, nitrogen atoms, aromatic rings and heterocyclic rings, the oxidation products of said polymers and the quaternization products of said polymers. For example, such polymers are described in French patents 2,162,025 and 2,280,361, the disclosures of which are incorporated herein by reference;

(6) water-soluble polyamino amides which may be prepared via at least one polycondensation reaction of at least one acidic compound and at least one polyamine compound, wherein said polyamino amides may be crosslinked with at least one crosslinking agent chosen from epihalohydrins, diepoxides, dianhydrides, unsaturated dianhydrides, bis-unsaturated derivatives, bis-halohydrins, bis-azetidiniums, bis-haloacyldiamines, bis-alkyl halides and oligomers derived from reaction of at least one difunctional compound with at least one compound chosen from bis-halohydrins, bis-azetidiniums, bis-haloacyidiamines, bis-alkyl halides, epihalohydrins, diepoxides and bis-unsaturated derivatives, wherein said crosslinking agent may be used in a proportion generally ranging from 0.025 mol to 0.35 mol per amine group of said polyamino amide, wherein said polyamino amides may optionally be alkylated, and wherein if said polyamino amides comprise at least one tertiary amine group, said polyamino amides may optionally be quaternized. For example, such polymers are described in French patents 2,252,840 and 2,368,508, the disclosures of which are incorporated herein by reference;

(7) polyamino amide derivatives derived from condensation of at least one polyalkylene polyamine with at least one polycarboxylic acid, followed by alkylation with at least one difunctional agent. Non-limiting examples of such polyamino amide derivatives include adipic acid/dialkylaminohydroxyalkyldialkylenetriamine polymers wherein the alkyl group comprises from 1 to 4 carbon atoms, such as methyl groups, ethyl groups and propyl groups. For example, such polymers are described in French patent 1,583,363, the disclosure of which is incorporated herein by reference.

Other non-limiting examples of such derivatives include the adipic acid/dimethylaminohydroxypropyl/diethylenetriamine polymers sold under the name "Cartaretine F, F4 or F8" by the company Sandoz.

(8) polymers derived from reaction of (i) at least one polyalkylene polyamine comprising two primary amine groups and at least one secondary amine group with (ii) at least one dicarboxylic acid chosen from diglycolic acid and saturated aliphatic dicarboxylic acids comprising from 3 to 8 carbon atoms. According to the present invention, the molar ratio of the at least one polyalkylene polyamine to the at least one dicarboxylic acid generally ranges from 0.8:1 to 1.4:1. The polyamino amide resulting from the above reaction may be reacted with epichlorohydrin in a molar ratio of epichlorohydrin to the at least one secondary amine group of the polyamino amide generally ranges from 0.5:1 to 1.8:1. For example, such polymers are described in U.S. Pat. Nos. 3,227,615 and 2,961,347, the disclosures of which are incorporated herein by reference.

Polymers of this type are sold, for example, under the name "Hercosett 57" by the company Hercules Inc. and under the name "PD 170" or "Delsette 101" by the company Hercules in the case of adipic acid/epoxypropyl/diethylenetriamine copolymers.

(9) cyclopolymers of alkyldiallylamine and cyclopolymers of dialkyldiallylammonium, such as homopolymers and copolymers comprising, as the main constituent of the chain, at least one unit chosen from units of formulae (V) and (VI):

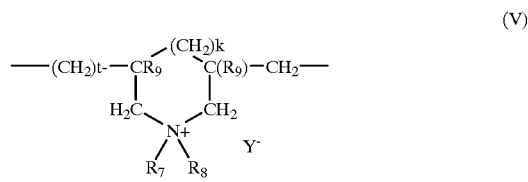

(V)

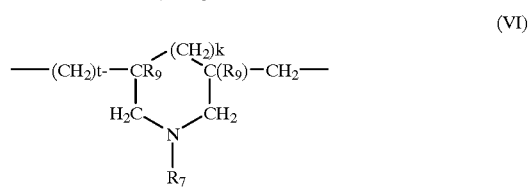

(VI)

wherein:
k and t, which may be identical or different, are each chosen from 0 and 1, with the proviso that the sum of k+t is equal to 1;

$R_9$, which may be identical or different, are each chosen from hydrogen atoms and methyl groups;

$R_7$ and $R_8$, which may be identical or different, are each chosen from alkyl groups comprising from 1 to 22 carbon atoms, hydroxyalkyl groups wherein the alkyl portion of said group optionally comprises from 1 to 5 carbon atoms, lower $C_1$–$C_4$ amidoalkyl groups, or $R_7$ and $R_8$, together with the nitrogen atom to which they are commonly attached, form at least one heterocyclic group, such as piperidyl groups and morpholinyl groups;

$Y^-$ is an anion, such as bromide, chloride, acetate, borate, citrate, tartrate, bisulphate, bisulphite, sulphate and phosphate. For example, such polymers are described in French patent 2,080,759 and in its Certificate of Addition 2,190,406, the disclosures of which are incorporated herein by reference.

In one embodiment, $R_7$ and $R_8$, which may be identical or different, are each chosen from alkyl groups comprising from 1 to 4 carbon atoms.

Non-limiting examples of the polymers defined above include the dimethyldiallylammonium chloride homopolymer sold under the name "Merquat 100" by the company Calgon (and its homologues of low weight-average molecular mass) and copolymers of diallyidimethylammonium chloride and of acrylamide, sold under the name "Merquat 550".

(10) quaternary diammonium polymers comprising at least two repeating units of formula:

(VII)

wherein:
$R_{10}$, $R_{11}$, $R_{12}$ and $R_{13}$, which may be identical or different, are each chosen from aliphatic groups comprising from 1 to 20 carbon atoms, alicyclic groups comprising from 3 to 20 carbon atoms, arylaliphatic groups comprising from 5 to 20 carbon atoms, lower hydroxyalkyl groups, and additionally, at least two of said $R_{10}$, $R_{11}$, $R_{12}$ and $R_{13}$, together with the nitrogen atoms to which they are attached, may form at least one heterocycle optionally comprising an additional heteroatom other than nitrogen, and additionally, $R_{10}$, $R_{11}$, $R_{12}$ and $R_{13}$, which may be identical or different, are each chosen from linear and branched $C_1$–$C_6$ alkyl groups substituted with at least one group chosen from nitrile groups, ester groups, acyl groups, amide groups and groups chosen from groups of formulae —CO—O—$R_{14}$—D and —CO—NH—$R_{14}$—D wherein $R_{14}$ is chosen from alkylene groups and D is chosen from quaternary ammonium groups;

$A_1$ and $B_1$, which may be identical or different, are each chosen from polymethylene groups comprising from 2 to 20 carbon atoms, chosen from linear and branched, saturated and unsaturated polymethylene groups wherein said polymethylene groups may optionally comprise, optionally linked to and optionally intercalated in the main chain, at least one entity chosen from aromatic rings, oxygen atoms, sulphur atoms, sulphoxide groups, sulphone groups, disulphide groups, amino groups, alkylamino groups, hydroxyl groups, quaternary ammonium groups, ureido groups, amide groups and ester groups; and X) is an anion chosen from anions derived from inorganic acids and anions derived from organic acids; and $A_1$, $R_{10}$ and $R_{12}$ may optionally form, together with the two nitrogen atoms to which they are attached, at least one piperazine ring;

with the proviso that if $A_1$ is chosen from linear and branched, saturated and unsaturated alkylene groups and linear and branched, saturated and unsaturated hydroxyalkylene groups, $B_1$ may also be chosen from groups of formula:

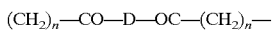

(CH$_2$)$_n$—CO—D—OC—(CH$_2$)$_n$— wherein;

n is a number such that the overall quaternary diammonium polymer has a number average molecular weight ranging from 1000 to 100,000; and D is chosen from:

a) glycol residues of formula: —O—Z—O—, wherein Z is chosen from linear and branched hydrocarbon groups and groups chosen from groups of formulae:

(CH$_2$—CH$_2$—O)$_x$—CH$_2$—CH$_2$—; and

[CH$_2$—CH(CH$_3$)—O]$_y$—CH$_2$—CH(CH$_3$)— wherein x and y, which may be identical or different, are each chosen from integers ranging from 1 to 4 (in which case x and y represent a defined and unique degree of polymerization) and any number ranging from 1 to 4 (in which case x and y represent an average degree of polymerization);

b) bis-secondary diamine residues such as piperazine derivatives;

c) bis-primary diamine residues chosen from residues of formula: —NH—Y—NH—, wherein Y is chosen from linear and branched hydrocarbon groups and residues of formula —CH$_2$—CH$_2$—S—S—CH$_2$—CH$_2$—; and d) ureylene groups of formula: —NH—CO—NH—.

In one embodiment, X⁻ is an anion chosen from chloride ions and bromide ions.

According to the present invention, the quarternary diammonium polymers have a number-average molecular mass generally ranging from 1000 to 100,000.

For example, polymers of this type are described in French Patent Nos. 2,320,330, 2,270,846, 2,316,271, 2,336,434 and 2,413,907 and U.S. Pat. Nos. 2,273,780, 2,375,853, 2,388,614, 2,454,547, 3,206,462, 2,261,002, 2,271,378, 3,874,870, 4,001,432, 3,929,990, 3,966,904, 4,005,193, 4,025,617, 4,025,627, 4,025,653, 4,026,945 and 4,027,020, the disclosures of which are incorporated herein by reference.

Further, according to the present invention, polymers comprising at least two repeating units of formula (VIII) may be used:

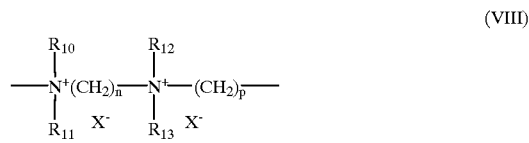

(VIII)

wherein:

$R_{10}$, $R_{11}$, $R_{12}$ and $R_{13}$, which may be identical or different, are each chosen from alkyl groups comprising from 1 to 4 carbon atoms and hydroxyalkyl groups comprising from 1 to 4 carbon atoms approximately;

n and p, which may be identical or different, are each chosen from integers ranging from 2 to 20 approximately; and X⁻ is an anion chosen from anions derived from inorganic acids and anoins derived from organic acids.

(11) Ammonium polymers comprising at least one unit of formula (IX):

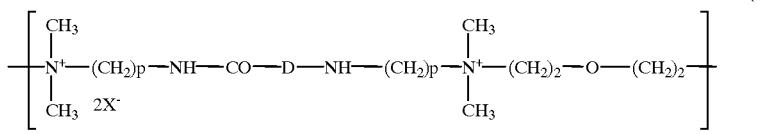

(IX)

wherein:

p, which may be identical or different, is chosen from integers ranging from 1 to 6, D is chosen from direct bonds and —(CH$_2$)$_r$—CO— groups wherein r is chosen from 4 and 7, and X⁻ is an anion chosen from anions derived from minerals and organic acids.

For example, the cationic compounds comprising units of formula (IX) are disclosed in patent application EP-A-122, 324, the disclosure of which is incorporated herein by reference, and may be prepared according to the processes disclosed in U.S. Pat. Nos. 4,157,388, 4,390,689, 4,702,906 and 4,719,282, the disclosures of which are incorporated herein by reference.

Non-limiting examples of ammonium polymers include those with a molecular weight, measured by carbon-13 NMR, of generally less than 100,000, and in formula (IX) wherein:

p is 3, and wherein a) D is a —$(CH_2)_4$—CO— group, $X^-$ is a chloride, and the molecular weight, measured by carbon-13 NMR ($C^{13}$ NMR), is generally about 5600; a polymer of this type, for example, is available from the company Miranol under the name Mirapol-AD1, b) D is a —$(CH_2)_7$—CO— group, $X^-$ is a chloride, and the molecular weight, measured by carbon-13 NMR ($C^{13}$ NMR) is generally about 8100; a polymer of this type, for example, is available from the company Miranol under the name Mirapol-AZ1, c) D is a direct bond, $X^-$ is a chloride, and the molecular weight, measured by carbon-13 NMR ($C^{13}$ NMR), is generally about 25,500; a polymer of this type, for example, is available from the company Miranol under the name Mirapol-A15, d) a "block copolymer" formed from units chosen from polymers described in paragraphs a) and c); polymers of this type, for example, are available from the company Miranol under the names Mirapol-9 ($C^{13}$ NMR molecular weight of generally about 7800), Mirapol-175 ($C^{13}$ NMR molecular weight of generally about 8000), and Mirapol-95 ($C^{13}$ NMR molecular weight of generally about 12 500).

Another embodiment of the invention is a polymer comprising units of formula (IX) wherein p is 3, D is a direct bond, $X^-$ is a chloride, and the molecular weight, measured by carbon-13 NMR ($C^{13}$ NMR), is generally about 25,500.

(12) quaternary polymers of vinylpyrrolidone and quaternary polymers of vinylimidazole, such as, for example, the products sold under the names Luviquat FC 905, FC 550 and FC 370 by the company BASF.

(13) polyamines, such as Polyquart H sold by Henkel under the reference name "Polyethylene glycol (15) Tallow polyamine" in the CTFA dictionary.

(14) crosslinked methacryloyloxy($C_1$–$C_4$)alkyltri($C_1$–$C_4$) alkylammonium salt polymers, such as the polymers derived from homopolymerization of dimethylaminoethyl methacrylate quaternized with methyl chloride and polymers derived from copolymerization, for example, of acrylamide with dimethylaminoethyl methacrylate quaternized with a with a methyl halide (such as methyl chloride), wherein the homo- or copolymerization is followed by crosslinking with at least one compound comprising olefinic unsaturation, such as methylenebisacrylamide. For example, a crosslinked acrylamide/methacryloyloxyethyltrimethylammonium chloride copolymer (20/80 by weight) in the form of a dispersion comprising 50% by weight of the said copolymer in mineral oil may be used. This dispersion is sold under the name "Salcare $SC_{92}$" by the company Allied Colloids. Further, a crosslinked methacryloyloxyethyltrimethylammonium chloride homopolymer comprising 50% by weight of the homopolymer in mineral oil or in a liquid ester may be used. These dispersions are sold under the names "Salcare SC 95" and "Salcare SC 96" by the company Allied Colloids.

Other cationic polymers which may be used as the at least one cationic polymer according to the present invention include polymers chosen from polyalkyleneimines (such as polyethyleneimines), polymers comprising at least one vinylpyridine unit, polymers comprising at least one vinylpyridinium unit, condensates of polyamines, condensates of epichlorohydrin, quaternary polyureylenes and chitin derivatives.

Other embodiments of the invention use cationic polymers chosen from the polymers of (1), (9), (10), (11) and (14). Specifically, polymers of formulae (W) and (U) can be used:

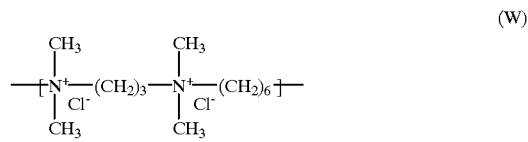
(W)

such as those of which the molecular weight, determined by gel permeation chromatography, generally ranges from 9500 to 9900;

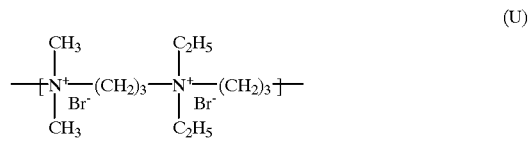
(U)

such polymers may also optionally include those wherein the molecular weight, determined by gel permeation chromatography, is generally 1200.

The at least one cationic polymer is present in an amount generally ranging from 0.01% to 10% by weight, such as from 0.05% to 5% by weight, and further such as from 0.1% to 3% by weight, relative to the total weight of the final composition.

The amphoteric polymers which may be used in accordance with the present invention may be chosen from polymers comprising K and M units distributed randomly in the polymer chain, wherein:

K is a unit derived from a monomer comprising at least one basic nitrogen atom and M is a unit derived from an acid monomer comprising at least one group chosen from carboxylic groups and sulphonic groups; or alternatively K and M, which may be identical or different, are derived from groups chosen from zwitterionic monomers of carboxybetaines and zwitterionic monomers of sulphobetaines; or alternatively K and M, which may be identical or different, are each chosen from polymers comprising cationic polymer chains comprising at least one amine group chosen from primary, secondary, tertiary and quaternary amine groups, wherein at least one of the amine groups is substituted with a group chosen from carboxylic groups and sulphonic groups linked via a hydrocarbon radical; or alternatively K and M form part of at least one chain of at least one polymer comprising at least one a,b-dicarboxylic ethylene unit wherein at least one of the carboxylic groups has been caused to react with at least one polyamine comprising at least one amine group chosen from primary amine groups and secondary amine groups.

Non-limiting examples of amphoteric polymers corresponding to the definition given above include:

(1) Polymers resulting from the copolymerization of a monomer derived from a vinyl compound substituted with at least one carboxylic group and of a basic monomer derived from a substituted vinyl compound comprising at least one basic atom.

Non-limiting examples of carboxylic groups used include carboxylic groups chosen from acrylic acid, methacrylic acid, maleic acid, and a-chloroacrylic acid.

Non-limiting examples of basic monomers used include those chosen from dialkylaminoalkyl methacrylate, dialkylaminoalkyl acrylate, dialkylaminoalkylmethacrylamide and dialkylaminoalkylacrylamide.

Such compounds are described, for example, in U.S. Pat. No. 3,836,537, the disclosure of which is incorporated herein by reference. Mention may also be made of the sodium acrylate/acrylamidopropyltrimethylammonium chloride copolymer sold under the name Polyquart KE 3033 by the company Henkel.

The vinyl compound may also be a dialkyldiallylammonium salt such as, for example, dimethyidiallylammonium chloride. Non-limiting examples of the copolymers of acrylic acid and of the latter monomer include those sold under the names Merquat 280, Merquat 295 and Merquat Plus 3330 by the company Calgon.

(2) Polymers comprising at least one unit derived from:
a) at least one monomer chosen from acrylamides substituted on the nitrogen with an alkyl radical and methacrylamides substituted on the nitrogen with an alkyl radical,
b) at least one acidic comonomer comprising at least one reactive carboxylic group, and
c) at least one basic comonomer such as, for example, comonomers chosen from esters of acrylic acid and esters of methacrylic acid, said esters being substituted with at least one amine chosen from primary, secondary, tertiary, and quaternary amines, and products of quaternization of dimethylaminoethyl methacrylate with at least one sulphate chosen from dimethyl suplhate and diethyl sulphate.

Some embodiments according to the invention utilize N-substituted acrylamides and methacrylamides comprising $(C_2-C_{12})$alkyl groups such as N-ethylacrylamide, N-tert-butylacrylamide, N-tert-octylacrylamide, N-octylacrylamide, N-decylacrylamide, N-dodecylacrylamide as well as the corresponding methacrylamides.

Non-limiting examples of acidic comonomers include acidic comonomers chosen from acrylic acid, methacrylic acid, crotonic acid, itaconic acid, maleic acid and fumaric acid and $(C_1-C_4)$alkyl monoesters, chosen from maleic acid, fumaric acid, maleic anhydride and fumaric anhydride.

Non-limiting examples of basic comonomers include basic comonomers chosen from methacrylates of aminoethyl, butylaminoethyl, N,N'-dimethylaminoethyl and N-tert-butylaminoethyl.

Further non-limiting examples include copolymers having the CTFA (4th edition, 1991) name octylacrylamide/acrylates/butylaminoethyl methacrylate copolymer such as, for example, the products sold under the name Amphomer or Lovocryl 47 by the company National Starch.

(3) Partially and completely crosslinked and alkylated polyamino amides partially derived from polyamino amides of formula:

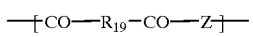

(X)

wherein:
$R_{19}$ is a divalent group derived from compounds chosen from: saturated dicarboxylic acids, dicarboxylic aromatic acids, carboxylic aliphatic acids chosen from monocarboxylic aliphatic acids and dicarboxylic aliphatic acids comprising at least one ethylenic double bond, and esters of $(C_1-C_6)$alkanols of said acids, and $R_{19}$ is also a divalent group derived from the addition of any one of the aforementioned acids with an amine chosen from bis(primary) and bis(secondary) amines, and Z is a divalent group derived from polyalkylene-polyamines chosen from bis(primary), mono- and bis(secondary) polyalkylene-polyamines. Non-limiting examples include:
a) in amounts generally ranging from 60 to 100 mol %, the group

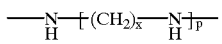

(XI)

wherein x=2 and p=2 or 3, or alternatively x=3 and p=2
wherein group Z is derived from a compound chosen from diethylenetriamine, triethylenetetraamine and dipropylenetriamine;
b) in an amount generally ranging from 0 to 40 mol %, (1) said groups (XI) above wherein x=2 and p=1, and which said group is derived from at least one compound chosen from ethylenediamine, and (2) groups derived from piperazine:

c) in an amount generally ranging from 0 to 20 mol %, the group $-NH-(CH_2)_6-NH-$, derived from hexamethylenediamine, wherein these polyamino amines are crosslinked by adding at least one bifunctional crosslinking agent (chosen from epihalohydrins, diepoxides, dianhydrides and bis-unsaturated derivatives), present in an amount generally ranging from 0.025 to 0.35 mol of crosslinking agent per amine group of the polyamino amide and alkylated by the action of at least one compound chosen from acrylic acid, chloroacetic acid and alkane sultones, and salts of said alkane sultones.

The saturated dicarboxylic acids are for example chosen from saturated $(C_6-C_{10})$ dicarboxylic acids such as adipic, 2,2,4-trimethyladipic and 2,4,4-trimethyladipic acid. Representative dicarboxylic aromatic acids include for example $(C_6-C_{10})$ dicarboxylic aromatic acids, such as terephthalic acid. And representative mono- and dicarboxylic aliphatic acids comprising at least one ethylenic double bond include for example acrylic, methacrylic and itaconic acids.

The alkane sultones used in the alkylation may optionally be chosen from propane sultone and butane sultone, and the salts of the alkylating agents can be chosen from sodium and potassium salts of said alkylating agents.

(4) Polymers comprising at least one zwitterionic unit of formula:

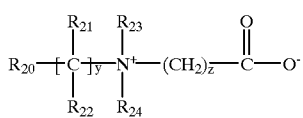

(XII)

wherein:

- $R_{20}$ is chosen from polymerizable unsaturated groups such as, for example, acrylates, methacrylates, acrylamides, and methacrylamides,
- y and z, which may be identical or different, are each chosen from integers ranging from 1 to 3,
- $R_{21}$ and $R_{22}$, which may be identical or different, are each chosen hydrogen and methyl, ethyl, and propyl groups,
- $R_{23}$ and $R_{24}$, which may be identical or different, are each chosen from hydrogen and alkyl groups, provided that the sum of the carbon atoms in $R_{23}$ and $R_{24}$ does not exceed 10.

The polymers comprising such zwitterionic units may also comprise at least one unit derived from non-zwitterionic monomers, such as units chosen from dimethylaminoethyl acrylate, dimethylaminoethyl methacrylate, diethylaminoethyl acrylate, diethylaminoethyl methacrylate, alkyl acrylates, alkyl methacrylates, alkyl acrylamides, alkyl methacrylamides 401 and vinyl acetate.

Other non-limiting examples include the copolymer of methyl methacrylate/dimethyl carboxymethylammonio methyl ethylmethacrylate such as the product sold under the name Diaformer Z301 by the company Sandoz.

(5) Polymers derived from chitosan comprising at least one monomeric unit chosen from formulae (XIII), (XIV) and (XV):

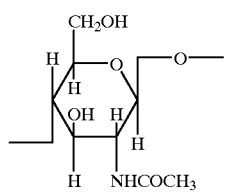
(XIII)

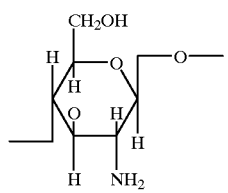
(XIV)

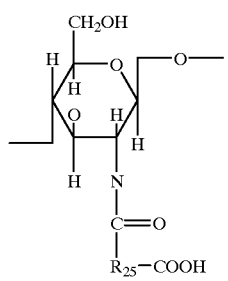
(XV)

wherein the unit (XIII) is present in an amount generally ranging from 0% to 30%, by weight relative to the total weight of said polymer, the unit (XIV) being present in proportions generally ranging from 5% to 50%, by weight relative to the total weight of said polymer, and the unit F being present in proportions generally ranging from 30% to 90%, by weight relative to the total weight of said polymer, and wherein in said unit (XV), $R_{25}$ chosen from groups of formula:

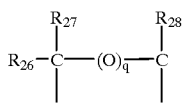

wherein:

q is equal to 0 or 1, and (i) when q is equal to 0, $R_{26}$, $R_{27}$ and $R_{28}$, which may be identical or different, are each chosen from hydrogen, methyl groups, hydroxyl groups, acetoxy groups, amino groups, monoalkylamine groups, dialkylamine groups and alkylthio groups, provided that at least one of the $R_{26}$, $R_{27}$ and $R_{28}$ groups is hydrogen;

When monoalkylamine and dialkylamine groups are used they may be optionally interrupted by at least one nitrogen atomn and/or optionally substituted with at least one group chosen from amine, hydroxyl, carboxyl, alkylthio and sulphonic groups.

When alkylthio groups are used, the alkyl portion of said alkylthic group carries an amino group; and (ii) when q is equal to 1, $R_{26}$, $R_{27}$ and $R_{28}$ are each chosen from hydrogen;

Other non-limiting examples include the salts formed by these polymers (5) with bases and acids.

(6) Polymers derived from the N-carboxyalkylation of chitosan, such as, for example, N-carboxymethylchitosan and N-carboxybutylchitosan sold under the name "Evalsan " by the company Jan Dekker.

(7) Polymers of the formula (XVI), which are described, for example, in French patent 1,400,366, the disclosure of which is incorporated herein by reference:

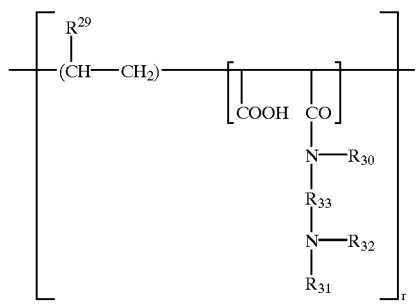
(XVI)

wherein:

r is chosen such that the number average molecular weight of said polymer ranges from 500 to 6,000,000, such as from 1,000 to 1,000,000;

$R_{29}$ is chosen from hydrogen, $CH_3O$, $CH_3CH_2O$ and phenyl groups;

$R_{30}$ is chosen from hydrogen and lower alkyl groups such as, for example, methyl and ethyl groups (as used herein, the term "lower alkyl" means a $C_1$–$C_6$ alkyl);

$R_{31}$ is chosen from hydrogen and lower alkyl groups such as, for example, methyl and ethyl groups;

$R_{32}$ is chosen from lower alkyl groups such as, for example, methyl and ethyl groups, and groups of the formula: —$R_{33}$—N($R_{31}$)$_2$, wherein $R_{33}$ is chosen from —CH$_2$—CH$_2$—, —CH$_2$—CH$_2$—CH$_2$— and —CH$_2$—CH(CH$_3$)— groups and $R_{31}$ is defined above;

Other examples include the higher homologues of these groups including higher homologues comprising up to 6 carbon atoms.

(8) Amphoteric polymers of the type —D—X—D—X chosen from:

a) polymers derived from the reaction of at least one compound chosen from chloroacetic acid and sodium chloroacetate with at least one compound comprising at least one unit of formula (XVI I):

  (XVII)

wherein D is a group:

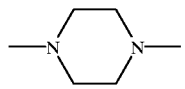

and X is chosen from the symbols E and E', which may be identical or different, wherein E and E' are each chosen from bivalent groups chosen from alkylene groups comprising at least one chain chosen from linear and branched chains comprising up to 7 carbon atoms in the principal chain, and wherein at least one chain may be optionally substituted with at least one hydroxyl group and may comprise 1 to 3 rings chosen from aromatic and heterocyclic rings, and may optionally comprise at least one atom chosen from oxygen, nitrogen and sulphur atoms; wherein:

the at least one optional atom is present in the form of at least one group chosen from ether, thioether, sulphoxide, sulphone, sulphonium, alkylamine alkenylamine, hydroxyl, benzylamine, amine oxide, quaternary ammonium, amide, imide, alcohol, ester and urethane groups.

b) Polymers of formula:

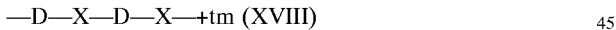 (XVIII)

wherein D is:

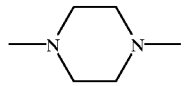

and X is chosen from the symbols E and E' and wherein at least one X is chosen from E' wherein:

E is chosen from bivalent groups chosen from alkylene groups comprising at least one chain chosen from linear and branched chains comprising up to 7 carbon atoms in the principal chain, and wherein at least one chain may be optionally substituted with at least one hydroxyl group and may comprise 1 to 3 rings chosen from aromatic and heterocyclic rings, and may optionally comprise at least one atom chosen from oxygen, nitrogen and sulphur atoms; wherein:

the at least one optional atom is present in the form of at least one group chosen from ether, thioether, sulphoxide, sulphone, sulphonium, alkylamine alkenylamine, hydroxyl, benzylamine, amine oxide, quaternary ammonium, amide, imide, alcohol, ester and urethane groups, and E' is a bivalent group chosen from alkylene groups comprising at least one chain chosen from linear and branched chains comprising up to 7 carbon atoms in the principal chain, wherein said at least one chain is optionally substituted with at least one hydroxyl group and wherein said at least one chain comprises at least one nitrogen atom substituted with an alkyl chain, wherein said alkyl chain is optionally interrupted by an oxygen atom and, wherein said alkyl chain comprises at least one functional group chosen from carboxyl and hydroxyl functional groups, and wherein said at least one alkyl chain is betainized by reaction with a reactant chosen from chloroacetic acid and sodium chloroacetate.

(9) ($C_1$–$C_5$)alkyl vinyl etherimaleic anhydride copolymers partially modified by semiamidation with an N,N-dialkylaminoalkylamine such as, for example, N,N-dimethylaminopropylamine. These copolymers may also be partially modified by semiesterification with at least one N,N-dialkanolamine. These copolymers may additionally comprise other vinyl comonomers such as, for example, vinylcaprolactam.

For example, the amphoteric polymers of family (1) are utilized in certain embodiments of the invention.

According to the present invention, the at least one amphoteric polymer may be present in an amount generally ranging from 0.01% to 10% by weight, such as from 0.05% to 5% by weight and further such as from 0.1% to 3% by weight, relative to the total weight of the composition.

The compositions of the invention may also comprise at least one surfactant.

The at least one surfactant chosen from anionic, amphoteric, nonionic, zwitterionic and cationic surfactants which are suitable for carrying out the present invention are, for example, the following:

(i) Anionic Surfactant(s):

to Representative anionic surfactants include salts (for example alkaline salts, such as sodium salts, ammonium salts, amine salts, amino alcohol salts and magnesium salts) of the following compounds: alkyl sulphates, alkyl ether sulphates, alkylamidoether sulphates, alkylarylpolyether sulphates, monoglyceride sulphates; alkyl sulphonates, alkyl phosphates, alkylamide sulphonates, alkylaryl sulphonates, a-olefin sulphonates, paraffin sulphonates; ($C_6$–$C_{24}$) alkyl sulphosuccinates, ($C_6$–$C_{24}$) alkyl ether sulphosuccinates, ($C_6$–$C_{24}$) alkylamide sulphosuccinates; ($C_6$–$C_{24}$) alkyl sulphoacetates; ($C_6$–$C_{24}$) acyl sarcosinates and ($C_6$–$C_{24}$) alkyl glutamates. Other representative examples include the carboxylic esters of ($C_6$–$C_{24}$) alkylpolyglycosides, such as alkylglucoside citrates, alkypolyglycoside tartrates and alkylpolyglycoside sulphosuccinates, alkylsulphosuccinamates, acyl isethionates and N-acyltaurates. The alkyl or acyl radical of all of these various compounds can, for example, comprise from 12 to 20 carbon atoms, and the aryl radicals can, for example, be chosen from phenyl and benzyl groups.

Other examples of anionic surfactants which may be used, include surfactants chosen from fatty acid salts such as the salts of oleic, ricinoleic, palmitic and stearic acids, coconut oil acid and hydrogenated coconut oil acid and acyl lactylates in which the acyl radical comprises from 8 to 20 carbon atoms. At least one weakly anionic surfactant can also be used, such as alkyl-D-galactosiduronic acids and their salts, polyoxyalkylenated ($C_6$–$C_{24}$) alkyl ether carboxylic acids, polyoxyalkylenated ($C_6$–$C_{24}$) alkylaryl ether carboxylic acids, polyoxyalkylenated ($C_6$–$C_{24}$) alkylamido ether carboxylic acids and their salts, for example, those comprising from 2 to 50 alkylene oxide groups, such as ethylene oxide groups.

(ii) Nonionic Surfactant(s):

Useful non-ionic surfactants include compounds that are well known per se (see for example in this respect "Handbook of Surfactants" by M. R. Porter, published by Blackie & Son (Glasgow and London), 1991, pp. 116–178) the disclosure of which is incorporated by reference herein, and, in the context of the present invention, their nature is not a critical feature. Thus, non-ionic surfactants can include polyethoxylated and polypropoxylated alkylphenols, a-diols and alcohols having a fatty chain comprising, for example, 8 to 18 carbon atoms, it being possible for the number of ethylene oxide and propylene oxide groups to range, for example, from 2 to 50. Mention may also be made of copolymers of ethylene oxide and of propylene oxide, condensates of ethylene oxide and of propylene oxide with fatty alcohols; polyethoxylated fatty amides for example comprising from 2 to 30 mol of ethylene oxide, polyglycerolated fatty amides comprising on average 1 to 5, such as from 1.5 to 4, glycerol groups; oxyethylenated fatty acid esters of sorbitan comprising from 2 to 30 mol of ethylene oxide; fatty acid esters of sucrose, fatty acid esters of polyethylene glycol, alkylpolyglycosides, N-alkylglucamine derivatives, amine oxides such as ($C_{10}$–$C_{14}$)alkylamine oxides and N-acylaminopropylmorpholine oxides. It will be noted that the alkylpolyglycosides are nonionic surfactants that can be suitable in the context of the present invention.

(iii) Amphoteric or Zwitterionic Surfactant(s):

Representative amphoteric or zwitterionic surfactants, whose nature is not a critical feature in the context of the present invention, can be chosen from aliphatic secondary and tertiary amine derivatives in which the aliphatic radical is chosen from linear and branched chain radicals comprising 8 to 18 carbon atoms and comprising at least one water-soluble anionic group (chosen, for example, from carboxylate, sulphonate, sulphate, phosphate and phosphonate); mention may also be made of ($C_8$–$C_{20}$) alkylbetaines, sulphobetaines, ($C_8$–$C_{20}$)alkylamido($C_1$–$C_6$) alkylbetaines and ($C_8$–$C_{20}$)alkylamido($C_1$–$C_6$) alkylsulphobetaines.

Representative amine derivatives include the products sold under the name Miranol, as described in U.S. Pat. Nos. 2,528,378 and 2,781,354, the disclosures of which are incorporated by reference herein, and classified in the CTFA dictionary, 3rd edition, 1982, under the names amphocarboxyglycinates and amphocarboxypropionates and having the structures:

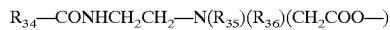

in which:

$R_{34}$ is chosen from alkyl groups derived from an acid $R_{34}$—COOH present in hydrolysed coconut oil, heptyl, nonyl and undecyl radicals, $R_{35}$ is chosen from b-hydroxyethyl groups, and $R_{36}$ is chosen from carboxymethyl groups; and

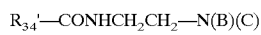

in which:

(B) is —$CH_2CH_2OX'$, wherein X' is an entity chosen from a —$CH_2CH_2$—COOH group and a hydrogen atom, (C) is —$(CH_2)_z$—Y', wherein z=1 or 2, and wherein Y' is an entity chosen from —COOH and —$CH_2$—CHOH—$SO_3H$ groups, $R_{34}'$ is chosen from alkyl groups such as (a) alkyl groups of an acid $R_{37}$—COOH present in oils chosen from coconut oil and hydrolysed linseed oil, (b) alkyl groups, such as $C_7$, $C_9$, $C_{11}$ and $C_{13}$ alkyl groups, and (c) $C_{17}$ alkyl groups and the iso form, and unsaturated $C_{17}$ groups.

Such representative compounds are classified in the CTFA dictionary, 5th edition, 1993, under the names disodium cocoamphodiacetate, disodium lauroamphodiacetate, disodium caprylamphodiacetate, disodium capryloamphodiacetate, disodium cocoamphodipropionate, disodium lauroamphodipropionate, disodium caprylamphodipropionate, disodium capryloamphodipropionate, lauroamphodipropionic acid and cocoamphodipropionic acid.

By way of example, mention may be made of the cocoamphodiacetate sold under the trade name Miranol® C2M Concentrate by the company Rhodia Chimie.

(iv) Cationic Surfactants:

Representative cationic surfactants include surfactants chosen from primary, secondary and tertiary fatty amine salts, optionally polyoxyalkylenated; quaternary ammonium salts such as tetraalkylammonium, alkylamidoalkyltrialkylammonium, trialkylbenzylammonium, trialkylhydroxyalkylammonium and alkylpyridinium chlorides and bromides; imidazoline derivatives; and amine oxides of cationic nature.

The amounts of surfactants present in the ready-to-use composition according to the invention may generally range from 0.01% to 40%, such as from 0.1% to 30% relative to the total weight of the composition.

The compositions according to the present invention may also comprise other agents for adjusting the rheology, such as, for example, cellulosic thickeners (chosen from hydroxyethylcellulose, hydroxypropylcellulose, carboxymethylcellulose, etc.), guar gum and its derivatives (chosen from hydroxypropyl guar, etc.), gums of microbial origin (chosen from xanthan gum, scleroglucan gum, etc.), synthetic thickeners such as crosslinked acrylic acid and acrylamidopropanesulphonic acid homopolymers and ionic and nonionic associative polymers such as the polymers sold under the names Pemulen TRI and TR2 by the company Goodrich, Salcare SC90 by the company Allied Colloids, Aculyn 22, 28, 33, 44 and 46 by the company Rohm & Haas, and Elfacos T210 and T212 by the company Akzo.

These additional thickeners can generally range from 0.05% to 10% by weight relative to the total weight of the composition.

The compositions according to the invention may also comprise at least one alkaline agent.

Representative basifying agents include, by way of example, those chosen from aqueous ammonia, ammonium chloride, alkali metal and alkaline-earth metal carbonates, alkali metal and alkaline-earth metal silicates, alkali metal and alkaline-earth metal phosphates, alkanolamines such as monoethanolamine, diethanolamine and triethanolamine and derivatives thereof, sodium hydroxide, potassium hydroxide and the compounds of formula (XIX) below:

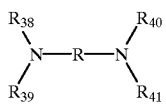

(XIX)

wherein:
  R is a propylene group optionally substituted with at least one group chosen from hydroxyl groups and $C_1$–$C_4$ alkyl groups;
  $R_{38}$, $R_{39}$, $R_{40}$ and $R_{41}$, which may be identical or different, are chosen from hydrogen, $C_1$–$C_4$ alkyl groups and $C_1$–$C_4$ hydroxyalkyl groups.

The compositions of the invention may also comprise at least one sequestering agent such as, for example, ethylenediaminetetraacetic acid (EDTA).

When the compositions comprising at least one oxidizing agent and at least one polymer with an aminoplast-ether skeleton are in anhydrous forms (for example powders and creams), they comprise the main agents and additives mentioned above in the form of essentially anhydrous solids and liquids. They may also comprise at least one filler chosen from mineral and organic fillers such as, for example, silica and clays. They may also comprise at least one binder such as those chosen from vinylpyrrolidone, oils and waxes, polyalkylene glycols and polyalkylene glycol derivatives. They may also comprise at least one lubricant such as, for example, those chosen from polyol stearates, alkali metal stearates, and alkaline-earth metal stearates, as well as dyes and matt-effect agents such as titanium oxides.

When the medium comprising the oxidizing agent is an aqueous medium, it may optionally comprise at least one cosmetically acceptable organic solvent chosen from, for example, alcohols such as ethyl alcohol, isopropyl alcohol, benzyl alcohol and phenylethyl alcohol, and glycols and glycol ethers such as, for example, ethylene glycol monomethyl, monoethyl and monobutyl ethers, propylene glycol and its ethers such as, for example, propylene glycol monomethyl ether, butylene glycol, dipropylene glycol and diethylene glycol alkyl ethers such as, for example, diethylene glycol monoethyl ether and monobutyl ether, in concentrations generally ranging from 0.5% to 20%, such as from 2% to 10% by weight relative to the total weight of the composition.

The bleaching composition according to the invention may also comprise an effective amount of at least one other agent chosen from various common adjuvants, for instance volatile and non-volatile, cyclic, linear and branched silicones that are organomodified (such as with amine groups) and non-organomodified, preserving agents, ceramides, plant, mineral and synthetic waxes and oils, acids such as AHA, etc.

Needless to say, a person skilled in the art would take care to select the optional additional compound(s) mentioned above such that the advantageous properties intrinsically associated with the bleaching composition according to the invention are not, or at least are not substantially, adversely affected by the addition(s) envisaged.

The pH of the ready-to-use composition generally ranges from 4 and 12, such as from 7 to 11.5, and further such as from 8 to 11.

The bleaching process according to the invention comprises, for example, applying the ready-to-use oxidizing composition to keratin fibers (which may optionally be wet or dry) and leaving the oxidizing composition to act for an exposure time generally ranging from 1 to 60 minutes, such as from 10 to 45 minutes, and rinsing the fibers, then optionally washing them with shampoo and then rinsing them again and drying them.

All numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the following specification and attached claims are approximations that may vary depending upon the desired properties sought to be obtained by the present invention. At the very least, and not as an attempt to limit the application of the doctrine of equivalents to the scope of the claims, each numerical parameter should be construed in light of the number of significant digits and ordinary rounding approaches.

Notwithstanding that the numerical ranges and parameters setting forth the broad scope of the invention are approximations, the numerical values set forth in the specific examples are reported as precisely as possible. Any numerical value, however, inherently contain certain errors necessarily resulting from the standard deviation found in their respective testing measurements. The following examples are intended to illustrate the invention without limiting the scope as a result.

EXAMPLE 1

The bleaching composition below (expressed in grams) was prepared:

| Anhydrous composition | |
|---|---|
| Potassium persulphate | 37 |
| Sodium persulphate | 30 |
| Sodium metasilicate | 12 |
| Ammonium chloride | 4 |
| EDTA | 1 |
| Sodium C16/C18 alkyl sulphate | 2 |
| Calcium stearate | 2 |
| Aculyn 44 (Rohm & Haas) | 0.8 AM* |
| Aculyn 46 (Rohm & Haas) | 1.2 AM* |
| Titanium dioxide | 2 |
| Clay | 8 |

40 g of the above anhydrous composition were mixed with 80 g of the following aqueous composition:

| Aqueous composition | |
|---|---|
| Cetearyl alcohol/ceteareth 30 | 2.85 |
| Stabilizers | 0.06 |
| Sequestering agent | 0.15 |
| 200-volumes hydrogen peroxide | 9 |
| Phosphoric acid    qs | pH 2 |
| Distilled water    qs | 100 |

A ready-to-use bleaching cream was thus obtained, which, when applied and left for 45 minutes under a hood, made it possible to obtain a powerful and homogeneous bleaching of natural dark hair.

EXAMPLE 2

The ready-to-use aqueous bleaching composition below (expressed in grams) was prepared:

| | |
|---|---|
| Cetearyl alcohol/ceteareth 30 | 2.2 |
| Aculyn 44 (Rohm & Haas) | 0.1 AM* |
| Aculyn 46 (Rohm & Haas) | 0.2 AM* |
| Stabilizers | qs |
| 30-volumes hydrogen peroxide | 18 |
| Phosphoric acid    qs | pH 2.5 |
| Distilled water    qs | 100 |

The above bleaching composition was applied and left for 45 minutes, under a hood, to natural hair and then rinsed out thoroughly with water. A uniform lightening of the hair was obtained.

What is claimed is:

1. A composition for bleaching keratin fibers comprising, in a medium appropriate for bleaching, at least one oxidizing agent, wherein said composition further comprises a combination of at least:
   one polyurethane polyether (a) which can be obtained by polycondensation of at least three compounds comprising (i) at least one polyethylene glycol comprising from 50 to 500 mol of ethylene oxide, (ii) at least one $C_8$–$C_{30}$ fatty alcohol, and (iii) at least one diisocyanate and,
   one polyurethane polyether (b) which can be obtained by polycondensation of at least three compounds comprising (i) at least one polyethylene glycol comprising from 50 to 500 mol of ethylene oxide, (ii) at least one $C_8$–$C_{30}$ fatty alcohol other than that of the at least one polyurethane polyether (a), and (iii) at least one diisocyanate.

2. A composition according to claim 1, wherein said keratin fibers are chosen from human keratin fibers.

3. A composition according to claim 2, wherein said human keratin fibers are chosen from human hair.

4. A composition according to claim 1, wherein in the at least one polyurethane polyether (a) and the at least one polyurethane polyether (b), the at least one polyethylene glycol is chosen from polyethylene glycols comprising 150 mol and 180 mol of ethylene oxide.

5. A composition according claim 1, wherein the at least one diisocyanate used to prepare the at least one polyurethane polyether (a) and the at least one polyurethane polyether (b) is methylenebis(4-cyclohexyl isocyanate).

6. A composition according to claim 1, wherein the $C_8$–$C_{30}$ fatty alcohol of the at least one polyisocyanate polyether (a) is stearyl alcohol.

7. A composition according to claim 1, wherein the at least one $C_8$–$C_{30}$ fatty alcohol of the at least one polyisocyanate polyether (b) is decyl alcohol.

8. A composition according to claim 1, wherein the at least one polyurethane polyether (a) is combined with a saccharide.

9. A composition according to claim 1, wherein the at least one polyurethane polyether (b) is combined with a saccharide.

10. A composition according to claim 8, wherein the saccharide is maltodextrin.

11. A composition according to claim 9, wherein the saccharide is maltodextrin.

12. A composition according to claim 1, wherein the at least one polyurethane polyether (a) is obtained by polycondensation of at least three compounds comprising at least one polyethylene glycol chosen from polyethylene glycols comprising 150 and 180 mol of ethylene oxide, stearyl alcohol and methylenebis(4-cyclohexyl isocyanate), and wherein the at least one polyurethane polyether (b) is obtained by polycondensation of at least three compounds comprising a polyethylene glycol chosen from polyethylene glycols comprising 150 and 180 mol of ethylene oxide, decyl alcohol and methylenebis(4-cyclohexyl isocyanate).

13. A composition according claim 1 wherein the weight ratio of the at least one polyurethane polyether (a) to the at least one polyurethane polyether (b) ranges from 0.1:1 to 10:1.

14. A composition according to claim 1, wherein the weight ratio of the at least one polyurethane polyether (a) to the at least one polyurethane polyether (b) ranges from 0.5:1 to 5:1.

15. A composition according to claim 1, wherein the at least one polyurethane polyether (a) is present in an amount ranging from 0.01% to 5% by weight, relative to the total weight of the composition.

16. A composition according to claim 1, wherein the at least one polyurethane polyether (a) is present in an amount ranging from 0.02% to 2% by weight, relative to the total weight of the composition.

17. A composition according to claim 1, wherein the at least one polyurethane polyether (b) is present-in an amount ranging from 0.01% to 5% by weight, relative to the total weight of the composition.

18. A composition according to claim 1, wherein the at least one polyurethane polyether (b) is present in an amount ranging from 0.02% to 2% by weight, relative to the total weight of the composition.

19. A composition according to claim 1, wherein the at least one oxidizing agent is chosen from hydrogen peroxide and compounds which release hydrogen peroxide by hydrolysis.

20. A composition according to claim 1, wherein the at least one oxidizing agent is chosen from urea peroxide, persalts, chlorites, enzymatic systems which generate oxidizing species, and organic peroxides.

21. A composition according to claim 20, wherein the persalts are chosen from alkali metals and alkaline-earth metal persulphates and perborates.

22. A composition according to claim 20, wherein the enzymatic systems are chosen from at least one two-electron oxidoreductase combined with its donor in the presence of air.

23. A composition according to claim 22, wherein the at least one two-electron oxidoreductase is uricase and its donor is uric acid.

24. A composition according to claim 19, wherein the hydrogen peroxide is present in an amount ranging from 2 to 40 volumes.

25. A composition according to claim 19, wherein the at least one oxidizing agent is present in an amount ranging from 0.1% to 25% by weight, relative to the total weight of the composition.

26. A composition according to claim 1, wherein said composition further comprises at least one direct dye.

27. A composition according to claim 1, wherein said composition further comprises at least one cationic polymer.

28. A composition according to claim 1, wherein said composition further comprises at least one amphoteric polymer.

29. A composition according to claim 27, wherein the at least one cationic polymer is a polyquaternary ammonium polymer comprising repeating units corresponding to formula (W) below:

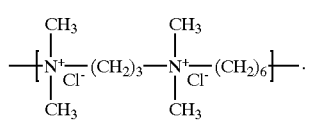

(W)

30. A composition according to claim 27, wherein the at least one cationic polymer is a polyquaternary ammonium polymer comprising repeating units corresponding to formula (U) below:

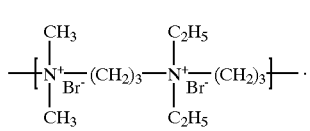

(U)

31. A composition according to claim 28, wherein the at least one amphoteric polymer chosen from copolymers comprising at least one acrylic acid monomer and at least one monomer chosen from dimethyldiallylammonium salts.

32. A composition according to claim 27, wherein the at least one cationic polymer is present in an amount ranging from 0.01% to 10% by weight, relative to the total weight of the composition.

33. A composition according to claim 27, wherein the at least one cationic polymer is present in an amount ranging from 0.05% to 5% by weight, relative to the total weight of the composition.

34. A composition according to claim 27, wherein the at least one cationic polymer is present in an amount ranging from 0.1% to 3% by weight, relative to the total weight of the composition.

35. A composition according to claim 28, wherein the at least one amphoteric polymer is present in an amount ranging from 0.01% to 10% by weight, relative to the total weight of the composition.

36. A composition according to claim 28, wherein the at least one amphoteric polymer is present in an amount ranging from 0.05% to 5% by weight, relative to the total weight of the composition.

37. A composition according to claim 28, wherein the at least one amphoteric polymer is present in an amount ranging from 0.01% to 3% by weight, relative to the total weight of the composition.

38. A composition according claim 1, wherein said composition further comprises at least one surfactant chosen from anionic, cationic, nonionic and amphoteric surfactants.

39. A composition according to claim 38, wherein the at least one surfactant is present in an amount ranging from 0.01% to 40% by weight, relative to the total weight of the composition.

40. A composition according to claim 38, wherein the at least one surfactant is present in an amount ranging from 0.1% to 30% by weight, relative to the total weight of the composition.

41. A composition according to claim 1, wherein said composition comprises at least one additional thickener.

42. A composition according to claim 41, wherein the at least one additional thickener is chosen from cellulose derivatives, guar derivatives, gums of microbial origin and synthetic thickeners.

43. A composition according to claim 41, wherein the at least one additional thickener is present in an amount ranging from 0.05% to 10% by weight, relative to the total weight of the composition.

44. A composition according to claim 1, wherein said composition also comprises at least one alkaline agent wherein said at least one alkaline agent is present in amounts ranging from 0.05% to 30% by weight, relative to the total weight of the composition.

45. A composition according to claim 44, wherein the at least one alkaline agent is chosen from aqueous ammonia, ammonium chloride, alkali metal and alkaline-earth metal carbonates, alkali metal and alkaline-earth metal silicates, alkali metal and alkaline-earth metal phosphates, alkanolamines, sodium hydroxide, potassium hydroxide and the compounds of formula (XIX) below:

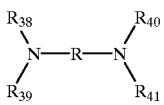

(XIX)

wherein:
R is chosen from propylene groups optionally substituted with at least one group chosen from hydroxyl groups and $C_1$–$C_4$ alkyl groups;
$R_{38}$, $R_{39}$, $R_{40}$ and $R_{41}$, which may be identical or different, are chosen from hydrogen, $C_1$–$C_4$ alkyl groups and $C_1$–$C_4$ hydroxyalkyl groups.

46. A composition according to claim 45, wherein the at least one alkaline agent is chosen from monoethanolamine, diethanolamine and triethanolamine and derivatives thereof.

47. A composition according to claim 1, wherein said composition is obtained by extemporaneous mixing, at the time of use, of (i) at least one anhydrous composition comprising at least one oxidizing agent and (ii) at least one aqueous composition, wherein at least one of said compositions chosen from compositions (i) and (ii) comprises the combination of the at least one polyurethane polyether (a) and the at least one polyurethane polyether (b).

48. A composition according to claim 47, wherein the at least one anhydrous composition is in pulverulent form.

49. A composition according to claim 47, wherein the at least one anhydrous composition comprises at least one additive chosen from:
mineral and organic fillers;
binders, oils and waxes, polyalkylene glycols and polyalkylene glycol derivatives;
lubricants; and
dyes and matt-effect agents.

50. A composition according to claim 49, wherein the at least one anhydrous composition comprises at least one additive chosen from silica and clays, vinylpyrrolidone, polyol stearates, alkali metal and alkaline-earth metal stearates, titanium oxides.

51. A composition according to claim 47, wherein each of said at least one additive is present in an amount ranging from 0% to 30% by weight, relative to the total weight of the composition.

52. A composition according to claim 1, wherein said composition is aqueous.

53. A composition according to claim 52, wherein the aqueous composition further comprises at least one organic solvent.

54. A composition according to claim 53, wherein the at least one organic solvent is present in amounts ranging from 0.5% to 20% by weight, relative to the total weight of the composition.

55. A composition according to claim 53, wherein the at least one organic solvent is present in amounts ranging from 2% to 10% by weight, relative to the total weight of the composition.

56. A composition according to claim 52, wherein the aqueous composition further comprises hydrogen peroxide.

57. A composition according to claim 1, wherein the composition has a pH ranging from 4 to 12.

58. A composition according to claim 1, wherein the composition has a pH ranging from 7 to 11.5.

59. A composition according to claim 1, wherein the composition has a pH ranging from 8 to 11.

60. A composition according to claim 47, wherein the combination of the at least one polyurethane polyether (a) and the at least one polyurethane polyether (b) is in an aqueous composition.

61. A process for bleaching keratin fibers comprising applying, in a medium appropriate for bleaching, a composition to said fibers, allowing the composition to act for an exposure time ranging from 1 to 60 minutes, rinsing the fibers, optionally washing the fibers with shampoo, after said optional washing, rinsing the fibers again and drying, and wherein said composition comprises at least one oxidizing agent, wherein said composition comprises a combination of at least:
   one polyurethane polyether (a) which can be obtained by polycondensation of at least three compounds comprising (i) at least one polyethylene glycol comprising from 50 to 500 mol of ethylene oxide, (ii) at least one $C_8$–$C_{30}$ fatty alcohol, and (iii) at least one diisocyanate and,
   one polyurethane polyether (b) which can be obtained by polycondensation of at least three compounds comprising (i) at least one polyethylene glycol comprising from 50 to 500 mol of ethylene oxide, (ii) at least one $C_8$–$C_{30}$ fatty alcohol other than that of the at least one polyurethane polyether (a), and (iii) at least one diisocyanate.

62. A bleaching process according to claim 61, wherein said keratin fibers are chosen from wet keratin fibers and dry keratin fibers.

63. A bleaching process according to claim 61, wherein said keratin fibers are chosen from human keratin fibers.

64. A bleaching process according to claim 61, wherein said human keratin fibers are chosen from human hair.

65. A device for bleaching keratin fibers comprising two compartments wherein:
   a first compartment comprises at least one composition chosen from powders and aqueous compositions,
   a second compartment comprises at least one aqueous composition,
   at least one of the two compartments comprises at least one oxidizing agent, and
   at least one of the two compartments comprises at least one composition comprising a combination of at least:
      one polyurethane polyether (a) which can be obtained by polycondensation of at least three compounds comprising (i) at least one polyethylene glycol comprising from 50 to 500 mol of ethylene oxide, (ii) at least one $C_8$–$C_{30}$ fatty alcohol, and (iii) at least one diisocyanate and,
      one polyurethane polyether (b) which can be obtained by polycondensation of at least three compounds comprising (i) at least one polyethylene glycol comprising from 50 to 500 mol of ethylene oxide, (ii) at least one $C_8$–$C_{30}$ fatty alcohol other than that of the at least one polyurethane polyether (a), and (iii) at least one diisocyanate.

66. A device according to claim 65, wherein said keratin fibers are chosen from human keratin fibers.

67. A device according to claim 66, wherein said human keratin fibers are chosen from human hair.

* * * * *

UNITED STATES PATENT AND TRADEMARK OFFICE
CERTIFICATE OF CORRECTION

PATENT NO.    : 6,444,197 B2
DATED         : September 3, 2002
INVENTOR(S)   : Frédéric Legrand It is certified that error appears in the above-identified patent and that said Letters Patent is hereby corrected as shown below:

Column 23,
Line 41, "according claim 1," should read -- according to claim 1, --.

Column 24,
Line 5, "according claim 1" should read -- according to claim 1, --.
Line 23, "present-in" should read -- present in --.

Column 25,
Line 47, "according claim 1," should read -- according to claim 1, --.

Signed and Sealed this

Eleventh Day of February, 2003

JAMES E. ROGAN
*Director of the United States Patent and Trademark Office*